United States Patent
Kim

[11] Patent Number: 5,441,540
[45] Date of Patent: Aug. 15, 1995

[54] METHOD AND APPARATUS FOR SKIN TISSUE EXPANSION

[76] Inventor: Paul S. Kim, 760 Drovers La., Chester Springs, Pa. 19425

[21] Appl. No.: 123,649

[22] Filed: Sep. 20, 1993

[51] Int. Cl.$^6$ .......................... A61F 2/02; A61F 2/10
[52] U.S. Cl. ........................................ 623/66; 623/11; 623/15; 606/216; 128/898
[58] Field of Search ............. 623/7, 8, 11, 15, 16, 623/66; 602/7, 9, 74; 606/55, 71, 78, 105, 132, 133, 144, 178, 210–218, 232, 241; 128/857, 862, 898, 899

[56] References Cited

U.S. PATENT DOCUMENTS

| | | | |
|---|---|---|---|
| 2,223,006 | 11/1940 | Laub | 606/216 |
| 3,650,274 | 3/1972 | Edwards et al. | 128/335 |
| 3,926,193 | 12/1975 | Hasson | 606/218 |
| 3,971,384 | 7/1976 | Hasson | 606/218 |
| 4,073,298 | 2/1978 | Le Roy | 606/216 |
| 4,512,346 | 4/1985 | Lemole | 606/216 |
| 4,535,772 | 8/1985 | Sheehan | 128/337 |
| 4,738,657 | 4/1988 | Hancock et al. | 604/93 |
| 4,798,584 | 1/1989 | Hancock et al. | 604/93 |
| 4,825,866 | 5/1989 | Pierce | 606/216 |
| 5,127,412 | 7/1992 | Cosmetto et al. | 128/898 |
| 5,183,059 | 2/1993 | Leonardi | 128/858 |
| 5,263,971 | 11/1993 | Hirshowitz et al. | 606/216 |

FOREIGN PATENT DOCUMENTS 1556666 4/1990 U.S.S.R. ............... 606/218

OTHER PUBLICATIONS

*Aesthetic and Reconstructive Surgery of the Scalp* by Toby G. Mayer and Richard W. Fleming, Mosby Year Book, Inc., © 1992 (Chapters 12 and 14 enclosed).
*J. Dermatol. Surg. Oncol.*, 1992; 18:112–123 by Bernard H. Cohen, M.D. and A. John Cosmetto entitled "The Suture Tension Adjustment Reel—A New Device for the Management of Skin Closure".
*Plast. Reconstr. Surg.*, 1992; 90:808–814 by Wee/-Logan/Mustoe, entitled "Continuous versus Intraoperative Expansion in the Pig Model".

Primary Examiner—David Isabella
Assistant Examiner—Laura Fossum
Attorney, Agent, or Firm—Synnestvedt & Lechner

[57] ABSTRACT

Utilizing the techniques of tissue expansion, hair-bearing scalp is created and/or wound closure is effected. Elongated anchor plates are implanted in the scalp at spaced apart locations. Each plate has projecting studs which are extended through incisions in the scalp. A readily attachable and removable skin tensioning means is attachable to the studs and set to the required tension for tissue expansion. Guide means control the force vector applied by the tensioning means to the anchor plates. The tensioning and guide means are attachable for use when the patient is in the privacy of his home. The tensioning means may comprise a pair of straps with a Velcro ® fastener, buckles or the like for the application of requisite tension at a controlled rate.

6 Claims, 3 Drawing Sheets

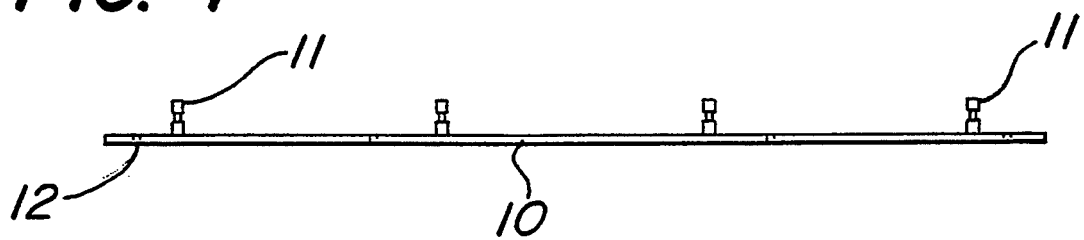
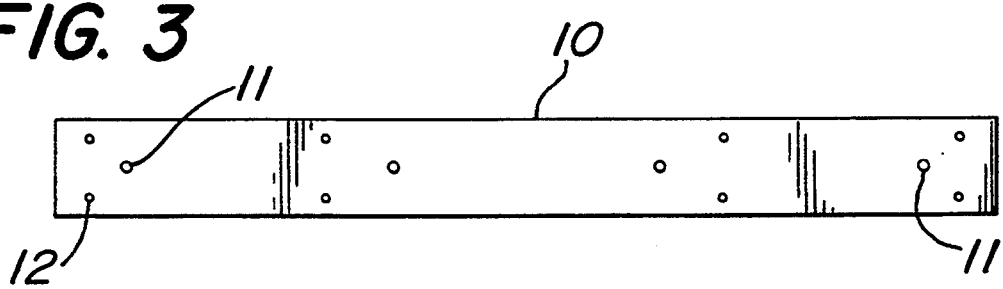
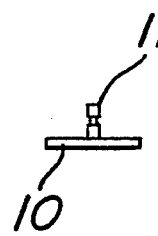
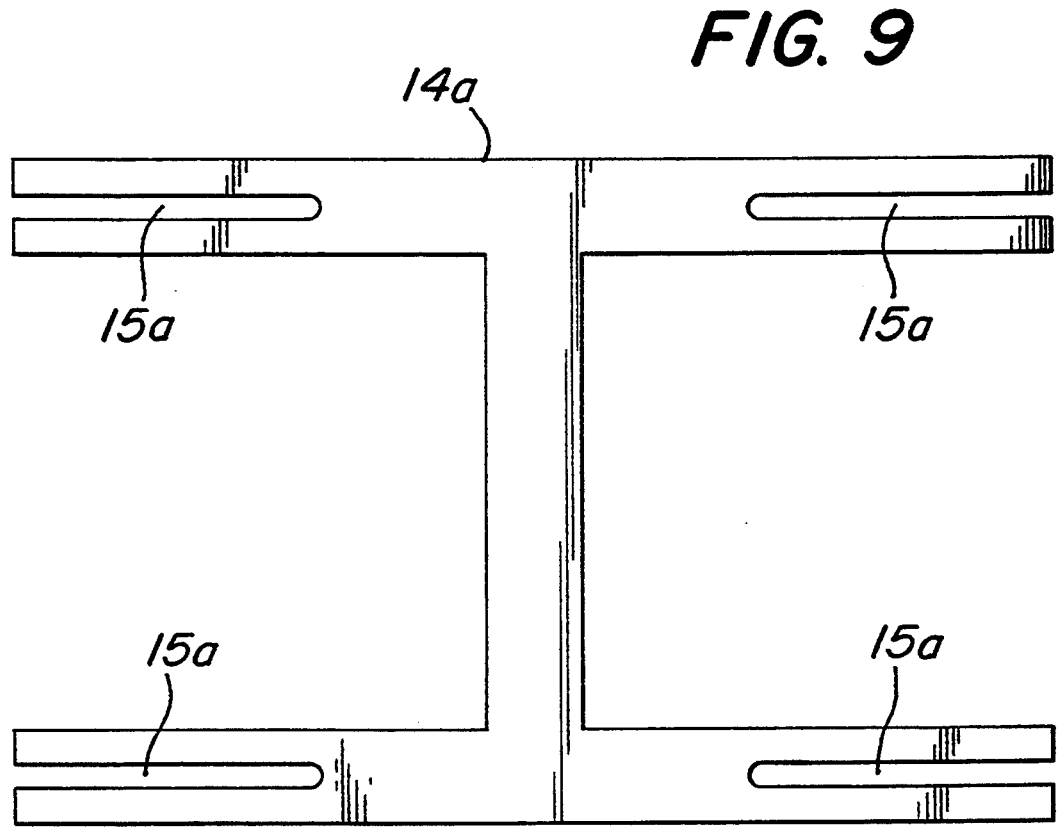

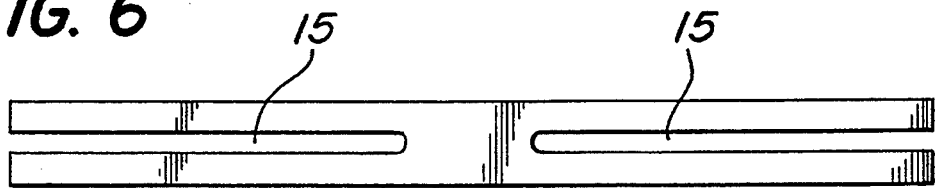
FIG. 6
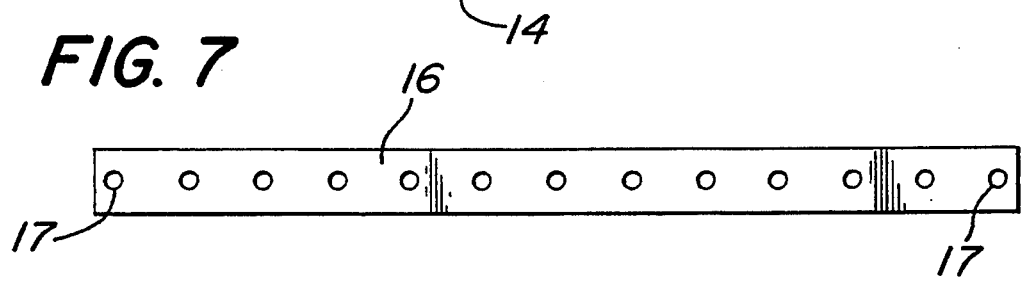
FIG. 7
FIG. 7A
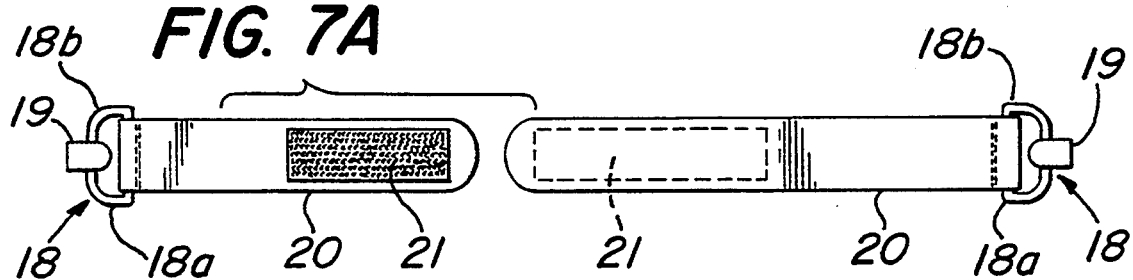
FIG. 8
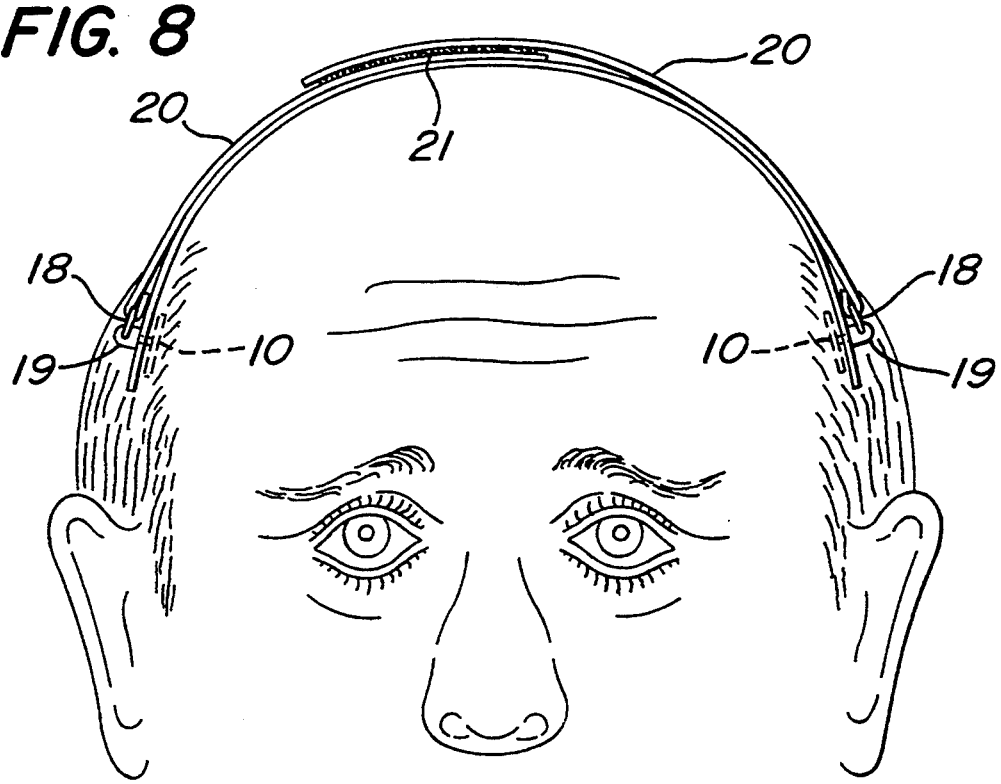

METHOD AND APPARATUS FOR SKIN TISSUE EXPANSION

FIELD OF THE INVENTION

This invention relates to the technique of tissue expansion and, more particularly, to methods and apparatus utilizing the principles of tissue expansion for the purpose of scalp reconstruction and more particularly for the creation of hair-bearing scalp. In its broadest aspects, the invention has applicability as well to the surgical closure of large skin wounds on other parts of the body and the replacement of skin defects.

BACKGROUND OF THE INVENTION

Tissue expansion is a known technique involving not merely the stretching of skin but the production of new skin. The process involves the use of the well known fact that skin, when placed under significant tension, will not only stretch but generate new skin which can be used for covering open wounds and other skin defects. In the treatment of baldness, particularly in the mid scalp and crown regions, the prior art teachings deemed most relevant involve the use of implantable tissue expander bags or balloons. These devices are implanted under hair-bearing portions of the scalp and are inflated with a liquid to expand an area of the scalp bearing relatively dense hair while not stretching an area of bald or sparse hair. A stretched flap of the skin bearing the relatively dense hair is then transposed and grafted to the area lacking hair after removal of a corresponding portion of the skin in the non-hair bearing region. A more detailed description of these techniques is found in the work Aesthetic and Reconstructive Surgery of the Scalp by Toby G. Mayer and Richard W. Fleming, Mosby Year Book, Inc., especially Chapters 12 and 14.

A related technique for tissue expansion which is described as useful in the preoperative expansion of skin tissue and also in the treatment of baldness is found in Cohen and Cosmetto, J. Dermatol. Surg. Oncol. 1992; 18:112-123. The devices utilized in the Cohen et al article are further described in U.S. Pat. No. 5,127,412, issued Jul. 7, 1992. The devices described in U.S. Pat. No. 5,127,412 comprise an anchor member positioned at one side of an incision and a ratcheting winder which draws a single loop of suture material across the incision, thus stretching the skin and/or closing a wound.

Although the techniques and equipment described just above are useful for the replacement of non-hair bearing scalp with hair-bearing scalp, problems exist which have hampered more wide spread acceptance. One problem with the balloon-type tissue expanders stems from the length of time that the devices must remain in place to complete the process. For the patient, this raises what is primarily a cosmetic problem. The time required may be as much as six to eight weeks, and especially during the later weeks, the effects of the tissue expansion process are difficult to conceal. The appearance of large, somewhat grotesque protuberances on the scalp, or even external tensioning devices, is impractical to disguise and, as a consequence, is something that many potential patients are unwilling to accept, especially since few people can avoid appearing in public for very long periods of time. In addition, during the period of tissue expansion, which averages about eight weeks, bi-weekly visits to the physician's office are necessary to complete the inflation process.

SUMMARY AND OBJECTS OF THE INVENTION

According to the invention, tissue expansion is accomplished by the implantation of anchor plates under the scalp tissue at oppositely disposed sides of a non-hair bearing region of the scalp. Each anchor plate is sutured to the scalp maintaining the plates in substantially parallel positions relative to each other under the scalp tissue. In a preferred embodiment of the invention, spaced projections extend from the upper surface of the plates through incisions through the scalp in the hair-bearing regions. An adjustable tensioning means, preferably removable by the patient at will without assistance from the surgeon, interconnects the projections on one anchor plate with the projections on the other anchor plate causing an expansion of tissue. Following removal of corresponding amounts of tissue in the non-hair bearing region, the expanded hair-bearing skin is extended into the non-hair bearing region. The process is repeated as often as necessary until the requisite amount of hair-bearing tissue replaces the non-hair bearing tissue.

In accordance with the invention, the adjustable tensioning means is reset by the patient undergoing treatment without the need for periodic visits to the physician's office. In a preferred form of the invention, the adjustable tensioning means is in the form of a device which can be removed by the patient in the privacy of his home. This allows the patient to remove the adjustable tensioning means when he is required to be in public. Since the projections are relatively hidden by the hair in the hair-bearing regions, the patient is able to carry on his day-to-day activities without feeling self conscious about the appearance of protuberances or of the adjustable means attached to his head. The tensioning means can be reapplied by the patient and retensioned so that the tissue expansion procedure can be continued at night or at other times in the privacy of the home of the patient.

An important object of the invention is the provision of apparatus and method of hair replacement which takes advantage of the phenomenon of tissue expansion by the application of tension to a predetermined region of the patient's scalp.

In accordance with the foregoing, it is an object of the invention to provide apparatus and method for the treatment of a non-hair bearing portion of the scalp of a patient which minimizes the appearance of disfigurement to which the patient is subjected during the tissue expansion process.

Another object of the invention is the provision of an apparatus and method of replacing a non-hair bearing region of the scalp with a hair-bearing region which permits adjustment by the patient so that the patient can choose both the time of day for use and the rate of tissue expansion in carrying out the hair replacement process.

A further object of the invention is the provision of a hair replacement method which substantially reduces the number of visits to the physician's office which must be made during the hair replacement procedure.

A still further object of the invention is the provision of a tissue expansion apparatus useful in hair replacement surgery, wound closure and reconstructive scalp surgery in which the principal portions of the apparatus disposed exteriorly of the scalp of the patient are readily removable and reattachable at will by the patient.

A still further object of the invention is the provision of an apparatus useful in tissue expansion in which novel guide means are provided for controlling the direction of application of the force vectors.

Other objects of the invention will become more fully apparent from the following detailed description of a preferred embodiment of the invention.

BRIEF DESCRIPTION OF THE DRAWINGS

FIG. 3 is a top view of an implantable anchor plate of the type shown schematically in FIGS. 1 and 2;

FIG. 4 is a side view of the anchor plate of FIG. 3;

FIG. 5 is an end view of the anchor plate of FIGS. 3 and 4;

FIG. 6 is a detail view of a preferred form of tensioning guide means utilized in carrying out the principles of the invention;

FIG. 7 is a view of an preferred form of tensioning device;

FIG. 7A is a view of an alternative form of a tensioning device; and

FIG. 8 is a schematic frontal view of the patient illustrating the assembly of anchor plates and the alternative form of guide and tensioning means of FIG. 7A.

FIG. 9 is an alternative form of the guide means.

DETAILED DESCRIPTION OF THE ILLUSTRATIVE EMBODIMENT OF THE INVENTION

Figure 1:
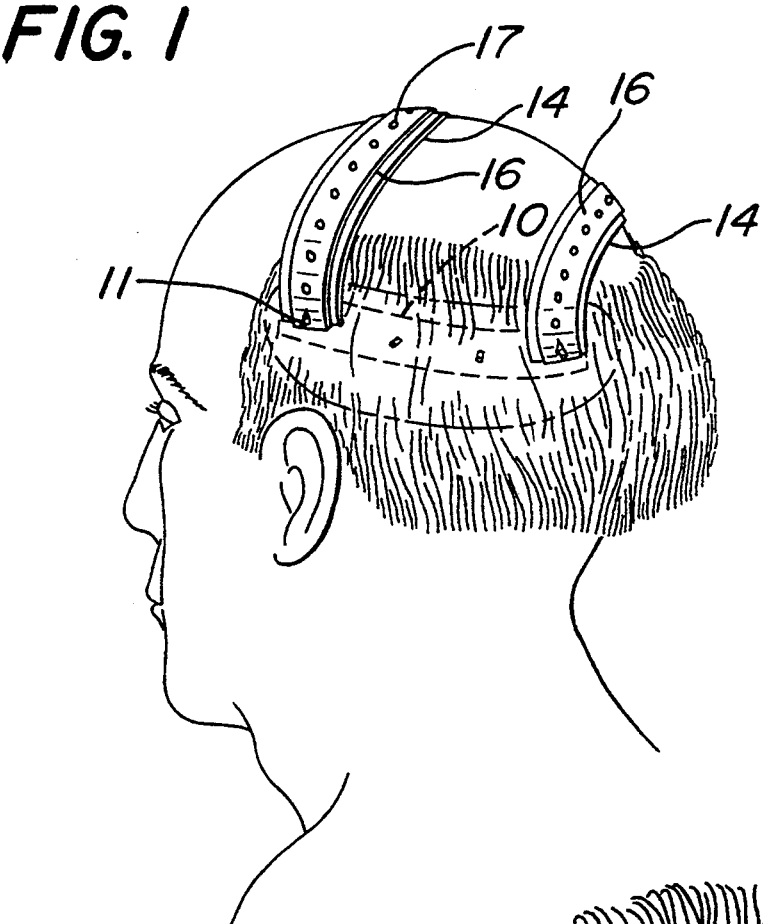
FIG. 1 is a side perspective view of the head of a patient illustrating the use of the apparatus and method of the present invention.

With reference to the drawings, apparatus used in carrying out the invention is comprised of three general components.

The first component comprises implantable means 40 which, in the preferred embodiment of the invention, as viewed in FIGS. 1-4, comprises a pair of base or anchor plates 10 which are inserted beneath the scalp just anterior of the balding hair line with each anchor plate 10 extended in a direction generally parallel to the other and to the edge of the non-hair bearing region which is intended to be replaced with hair-bearing scalp. Each anchor plate is provided with a plurality of projecting studs 11 disposed lengthwise thereof and spaced apertures 12 which are utilized to fasten the anchor plates 10 to the scalp by sutures, not shown. The anchor plates 10 are formed of a biologically inert material which is relatively flexible and malleable so as to be conformable to the contours of the skull of the patient. Known materials, such as stainless steel, titanium in metal form, polyurethane or polytetrafluoroethylene (PTFE), are in wide-spread use as materials for implantable devices and are suitable for the purpose. A preferred material is proprietary low-temperature thermoplastic material sold by WFR/AQUAPLAST CORP. of Wyckoff, N.J., under the trademark OPTIMOLD and available under Product Nos. 1622, 1722, 1822 or 1922. This thermoplastic becomes quite malleable at a temperature of about 200° F. and may be heated by the surgeon using a hot air dryer prior to the implant surgery to facilitate conforming the plate to the contour of the skull of the patient. Upon cooling, the material retains the shape to which it is conformed.

Figure 2:
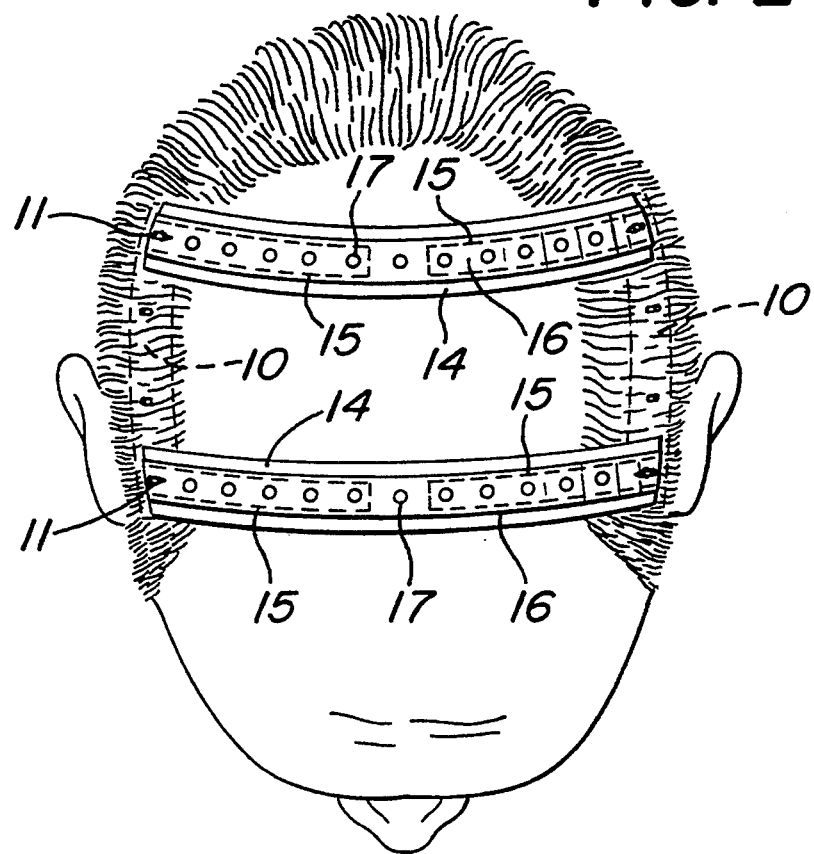
FIG. 2 is a top view of the head of a patient illustrating the apparatus and method of FIG. 1.

As can be seen in FIGS. 1, 2 and 8, each anchor plate 10 is inserted with the studs 11 projecting upwardly through an incision extending lengthwise of the border of the non-hair bearing region. The anchor plates 10 are then sutured to the hair-bearing region approximately 2 cm in from the edge of the incision using suture apertures 12. As the anchor plates 10 are inserted, the studs 11 are palpated through the hair-bearing scalp and a small stab incision is made at each stud location, thus allowing each stud to project through the scalp.

As is illustrated in FIG. 5, each stud 11 is preferably provided with a notch or circumferential groove for quick and easy attachment and detachment of the adjustable tensioning means, as described hereinafter.

After an appropriate time for the healing of the incisions, the tension applying components of the apparatus are installed so that skin expansion may take place. In carrying out this aspect of the invention, guide means comprising flexible, malleable guide plates 14 are shown in FIG. 6. The guide plates 14 have oppositely disposed guide slots 15 and are fitted over the patient's scalp with the studs 11 slidably interfitting within the slots 15. An alternative form of guide means, as illustrated in FIG. 9, comprises a single plate 14a having pairs of oppositely disposed slots 15a which receive the studs 11 at each end of scalp tissue to be treated. The guide means serves to resist any tendency of the anchor plates towards misalignment during the process of tension application. The guide means of FIG. 9 is preferably formed of a material which may be trimmed to final shape by the surgeon with a pair of sturdy shears so that the guide slots can be made to line up with the studs without binding or pulling on the scalp tissue.

The guide plates 14, 14a need not be biocompatible but should be flexible and malleable so as to allow for conformation to the contours of the skull, as can be seen in FIG. 8. In preferred form, the guide plates may be of the same material as the anchor plates. The material sold under the trademark OPTIMOLD is considered to be a preferred material in that it can be formed to the desired shape using an air dryer and can be easily trimmed to shape.

The third component of the overall apparatus is the tension applying means, perhaps best illustrated by reference to FIGS. 1, 2 and 7. Although various forms of tension applying means may be employed, the tension applying means should be simple to attach to the studs 11 and should provide for a quick and easy application of tension.

In a preferred form of the invention, the tension applying means comprises elastic bands 16 having a plurality of spaced apertures 17, as seen in FIGS. 1, 2 and 7. In an alternative arrangement, modified U-shaped rings 18 have a pair of resilient arms 18a and 18b which interfit within oppositely disposed openings in caps 19 which snap-fit onto studs 11. Each U-shaped ring 18 is secured to the end of a strap 20, each of which has a strip of fastener material 21, such as Velcro ® or like interengageable fastening means.

With the elastic band tensioning means, the patient adjusts the tension by choosing the appropriate aperture. In the alternative embodiment of FIGS. 7A and 8, the Velcro ® strips on the straps 20 are adjusted by the patient in a similar manner to apply the tension required to affect the requisite amount of tissue expansion.

With particular reference to FIGS. 1, 2 and 8 in carrying out the method, the anchor plates 10 are implanted as described above. Following a suitable period to allow for healing of the incisions, the tension guide means 14 and the elastic band 16 or the straps 20 are applied and the requisite tension set. If the patient must appear in public and is self conscious about the appearance of the apparatus, it is a simple matter to remove the tension guide means 14 and the tensioning means during the day, reapplying them when he returns to his home at night. As the scalp loosens over time, the individual periodically increases the tension in order to expand the skin in both the hair-bearing and non-hair bearing regions. When a predetermined amount of tissue expansion is effected, the patient returns to the surgeon for removal of the expanded non-hair bearing skin. Over a period of time, the entire non-hair bearing region can be replaced with hair-bearing tissue without removal of the anchor plates 10 until the expansion is complete.

As compared with inflatable balloon-type devices, large protuberances on the scalp of the patient are avoided, thereby leading to a great willingness on the part of the patient to accept the procedure. The patient himself has substantial control over the rate of scalp expansion. The patient can unself-consciously carry on the duties of his occupation since all portions of the apparatus can be removed, except for the implanted anchor plates, and the projections on these plates are relatively easily camouflaged in the hair-bearing regions of the scalp. If the studs are not readily camouflaged by rearrangement of the patient's hair, they may be effectively hidden by cutting portions of normal hair and adhesively securing the portions to caps formed of rubber or plastic which can then be fitted over the studs by the patient.

What is claimed:

1. Apparatus for reducing an area of a non-hair bearing area of a scalp overlying a skull of a patient in relation to hair bearing areas of the scalp extending along oppositely disposed side edges of the non-hair bearing area comprising:
   a pair of elongated anchor plates dimensioned and configured to be implanted under the scalp of the patient along the oppositely disposed edges of the non-hair bearing area;
   each of said anchor plates having suture anchor means for suturing the anchor plates to the scalp and further having spaced projections extending from an upper surface thereof, said spaced projections being dimensioned and configured to extend through incisions in the scalp;
   adjustable tensioning means interconnecting the projections on one of said anchor plates with the projections on the other of said anchor plates, said adjustable tensioning means applying tension to the anchor plates sufficient to produce a predetermined tissue expansion in hair and non-hair bearing regions; and
   guide plate means dimensioned and configured to be spaced exteriorly of the scalp, said guide plate means having a length extending at least from one of said anchor plates to the other of said anchor plates and further having oppositely disposed slots slidably engaging said spaced projections.

2. Apparatus according to claim 1, wherein said guide plate means comprises at least two interconnected members, each having oppositely disposed slots slidably engaging said spaced projections and extending in a direction of application of force by said adjustable tensioning means.

3. Apparatus according to claim 2, wherein said guide plate means is a heat settable thermoplastic material, said material being conformable to a shape of the patient's skull in response to temperatures of about 200 degrees F and being settable to maintain said shape upon return to ambient temperatures.

4. Apparatus according to claim 1, wherein said adjustable tensioning means comprises flexible straps attached to the projections on one of said anchor plates and an adjustable attachment means for attachment to a corresponding one of said projections on the other of said anchor plates.

5. Apparatus according to claim 1, wherein said adjustable tensioning means comprises a pair of flexible straps attached to corresponding oppositely disposed projections on said anchor plates, said straps including interengagable hook and loop fastener strips.

6. A kit for reducing an area of a non-hair bearing area of a scalp of a patient in relation to hair-bearing areas extending along oppositely disposed side edges on the non-hair bearing area comprising:
   a pair of elongated anchor plates dimensioned and configured to be implanted under the scalp of the patient along the oppositely disposed edges of the non-hair bearing area;
   each of said anchor plates having suture anchor means for suturing the anchor plates to the scalp and further having an upper surface with spaced projections therefrom, said spaced projections being dimensioned and configured to extend through incisions in the scalp;
   adjustable tensioning means interconnecting the projections on one of said anchor plates with the projections on the other of said anchor plates, said adjustable tensioning means applying tension to the anchor plates sufficient to produce a predetermined tissue expansion in hair and non-hair bearing areas; and
   a plate of substantially thin plastic material adapted to be trimmed to form longitudinally extending oppositely disposed slots, said plate being dimensioned and configured to extend a distance equal to a predetermined maximum spacing between said anchor plates when the anchor plates are inserted in the scalp of the patient for maintaining the tensioned anchor plates in a substantially parallel relationship.

* * * * *